United States Patent
Allison et al.

(10) Patent No.: US 6,200,562 B1
(45) Date of Patent: Mar. 13, 2001

(54) METHOD FOR REDUCING ABSORPTION OF DIETARY OXALATE USING ENZYMES AND MICROBES

(75) Inventors: Milton J. Allison, Ames, IA (US); Harmeet Sidhu, Gainesville, FL (US)

(73) Assignee: Ixion Biotechnology, Inc., Alachua, FL (US)

( * ) Notice: Subject to any disclaimer, the term of this patent is extended or adjusted under 35 U.S.C. 154(b) by 0 days.

(21) Appl. No.: 09/083,362

(22) Filed: May 22, 1998

Related U.S. Application Data

(60) Provisional application No. 60/047,473, filed on May 23, 1997.

(51) Int. Cl.[7] ............................. A01N 63/00; A61K 38/51
(52) U.S. Cl. ........................ 424/94.5; 424/93.1; 435/193; 435/196; 435/232
(58) Field of Search .................................. 424/94.5, 93.1; 435/196, 232, 193

(56) References Cited

U.S. PATENT DOCUMENTS

| 5,286,495 | 2/1994 | Batich et al. |
| 5,547,870 | * 8/1996 | Datta et al. ........................... 435/325 |
| 5,604,111 | * 2/1997 | Peck ....................................... 435/15 |

FOREIGN PATENT DOCUMENTS

| 9531537 | 11/1995 | (WO) . |
| 9535377 | 12/1995 | (WO) . |
| 9816632 | 4/1998 | (WO) . |

OTHER PUBLICATIONS

Lung, Hui–Yu et al. (1991) Cloning and expression of the oxalyl–CoA decarboxylase gene from the bacterium, *Oxalobacter formigenes*: prospects for gene therapy to control Ca–oxalate kidney stone formation American Journal of Kidney Disease Vo.I. XVII (4): 381–385.

Han, Jian–zhi et al. (1995) "The Relationship of *Oxalobacter Formigenes* and Calcium Oxalate Calculi" Journal of Tongji Medical University 15(4):249–252.

Daniel, Steven L., Paul A. Hartman, Milton J. Allison (1987) "Microbial Degradation of Oxalate in the Gastrointestinal Tracts of Rats" Applied and Environmental Microbiology 53(8): 1793–1797.

Dawson, Karl A., M.J. Allison, P.A. Hartman (1980) "Isolation and Some Characteristics of Anaerobic Oxalate–Degrading Bacteria from the Rumen"Applied and Environmental Microbiology 40(4):833–839.

Doane, Lori T., Michael Liebman, Daniel R. Caldwell (1989) "Microbial Oxalate Degradation: Effects On Oxalate And Calcium Balance In Humans" Nutrition Research 9:957–964.

Solomons, Clive C., M. Herzl Melmed, Susan M. Heitler (1991) "Calcium Citrate For Vulvar Vestibulitis" The Journal of Reproductive Medicine 36(12):879–882.

Sidhu, H., M.J. Allison, A.B. Peck (1996) "Detection and Characterization of *Oxalobacter formigenes* Strains Using Oligonucleotide Probes" Meeting for Urolithaisis, pp 537–539, Pak, C.Y.C. et al. (ed.).

Allison, M.J., H.M. Cook (1981) "Oxalate degradation by microbes of the large bowel of herbivores: the effect of dietary oxalate" Science 212:675–676.

Allison, Milton J., Karl A. Dawson, William R. Mayberry, John G. Foss (1985) "*Oxalobacter formigens* gen. nov., sp. now.: oxalate–degrading anaerobes that inhibit the gastrointestinal tract" Arch Microbiol 141:1–7.

Allison, Milton J., Herbert M. Cook, David B. Milne, Sandra Gallagher, Ralph V. Clayman (1986) "Oxalate Degradation by Gastrointestinal Bacteria from Humans" J. Nutr. 116:455–460.

Allison, Milton J., Steven L. Daniel, Nancy A. Cornick (1995) "Oxalate–Degrading Bacteria" In: Khan, S.R. (ed), Calcium Oxalate in Biological Systems CRC Press, Chapter 7, pp 131–168.

Daniel, S.L., P.A. Hartman, M.J. Allison (1993) "Intestinal Colonisation of Laboratory Rats by Anaerobic Oxalate–degrading Bacteria: Effects on the Urinary and Faecal Excretion of Dietary Oxalate" Microbial Ecology in Health and Disease 6:277–283.

Ito, Haruo, Masami Miyake, Masatoshi Noda (1995) "A New Oxalate–degrading Organism Isolated from Human Feces" Abstr. Annual Meeting Amer. Soc. Microbiol. Q–106.

Jensen, Neil S., Milton J. Allison (1994) "Studies on the Diversity Among Anaerobic Oxalate Degrading Bacteria now in the Species *Oxalobacter formigenes*" Abstr. General Meeting of the American Soc. Microbiol. I–12.

* cited by examiner

Primary Examiner—Leon B. Lankford, Jr.
(74) Attorney, Agent, or Firm—Saliwanchik, Lloyd & Saliwanchik

(57) ABSTRACT

This invention provides materials and procedures for the delivery of selected strains of bacteria and/or oxalate-degrading enzymes to the intestinal tracts of persons who are at increased risk for oxalate related disease because they have lost, or have inadequate concentrations of these bacteria. The administration of these bacteria and/or the relevant enzyme removes oxalate from the intestinal tract and thus reduces the amount of oxalate available for absorption and reduces the risk for oxalate related disease.

12 Claims, 5 Drawing Sheets

METHOD FOR REDUCING ABSORPTION OF DIETARY OXALATE USING ENZYMES AND MICROBES

CROSS-REFERENCE TO RELATED APPLICATION

This application claims priority from provisional application U.S. Ser. No. 60/047,473, filed May 23, 1997.

BACKGROUND OF THE INVENTION

Kidney-urinary tract stone disease (urolithiasis) is a major health problem throughout the world. Most of the stones associated with urolithiasis are composed of calcium oxalate alone or calcium oxalate plus calcium phosphate. Other disease states have also been associated with excess oxalate. These include, vulvodynia, oxalosis associated with end-stage renal disease and with Crohn's disease, and other enteric disease states.

Oxalic acid (and/or its salt-oxalate) is found in a wide diversity of foods, and is therefore, a component of many constituents in human diets. Increased oxalate absorption may occur after foods containing elevated amounts of oxalic acid are eaten. Foods such as spinach and rhubarb are well known to contain high amounts of oxalate, but a multitude of other foods and beverages also contain oxalate. Because oxalate is found in such a wide variety of foods, diets that are low in oxalate and which are also palatable are hard to formulate.

Oxalate is also produced metabolically by normal tissue enzymes. Oxalate (dietary oxalate that is absorbed as well as oxalate that is produced metabolically) is not further metabolized by tissue enzymes and must therefore be excreted. This excretion occurs mainly via the kidneys. The concentration of oxalate in kidney fluids is critical, with increased oxalate concentrations causing increased risk for the formation of calcium oxalate crystals and thus the subsequent formation of kidney stones.

The risk for formation of kidney stones revolves around a number of factors that are not yet completely understood. Kidney-urinary tract stone disease occurs in about 2% of the population in Western countries and about 70% of these stones are composed of calcium oxalate or of calcium oxalate plus calcium phosphate. Some individuals (e.g., patients with intestinal disease such as Crohn's disease, inflammatory bowel disease, or steatorrhea and also patients that have undergone jejunoileal bypass surgery) absorb more of the oxalate in their diets than do others. For these individuals, the incidence of oxalate urolithiasis increases markedly. The increased disease incidence is due to increased levels of oxalate in kidneys and urine, and this, the most common hyperoxaluric syndrome in man, is known as enteric hyperoxaluria. Oxalate is also a problem in patients with end-stage renal disease and there is recent evidence (Solomons et al. [1991] "Calcium citrate for vulvar vestibulitis" *Journal of Reproductive Medicine* 36:879–882) that elevated urinary oxalate is also involved in vulvar vestibulitis (vulvodynia).

Bacteria that degrade oxalate have been isolated from human feces (Allison et al. [1986] "Oxalate degradation by gastrointestinal bacteria from humans" *J. Nutr.* 116:455–460). These bacteria were found to be similar to oxalate-degrading bacteria that had been isolated from the intestinal contents of a number of species of animals (Dawson et al. [1980] "Isolation and some characteristics of anaerobic oxalate-degrading bacteria the rumen"*Appl. Environ. Microbiol.* 40:833–839;Allison and Cook [1981] "Oxalate degradation by microbes of the large bowel of herbivores: the effect of dietary oxalate" *Science* 212:675–676; Daniel et al. [1987] "Microbial degradation of oxalate in the gastrointestinal tracts of rats" *Appl. Environ. Microbiol.* 53:1793–1797). These bacteria are different from any previously described organism and have been given both a new species and a new genus name, formigenes (Allison et al. [1985] "*Oxalabacter formigenes* gen. nov., sp. nov.: oxalate-degrading anaerobes that inhabit the gastrointestinal tract" *Arch. Microbiol.* 141:1–7).

Not all humans carry populations of *O. formigenes* in their intestinal tracts (Allison et al. [1995] "Oxalate-degrading bacteria"In Khan, S. R. (ed.), *Calcium Oxalate in Biological Systems* CRC Press; Doane et al. [1989] "Microbial oxalate degradation: effects on oxalate and calcium balance in humans" *Nutrition Research* 9:957–964). There are very low concentrations or a complete lack of oxalate degrading bacteria in the fecal samples of persons who have had jejunoileal bypass surgery (Allison et al. [1986] "Oxalate degradation by gastrointestinal bacteria from humans" *J. Nutr.* 116:455–460).

BRIEF SUMMARY OF THE INVENTION

The subject invention pertains to materials and methods which reduce the risk for developing urolithiasis by limiting the amount of dietary oxalate absorbed from the intestinal tract. In one embodiment of the subject invention, a reduction in oxalate absorption is achieved by supplying oxalate-degrading bacteria to the intestinal tract. In a preferred embodiment, these bacteria are *Oxalobacter formigenes*. These bacteria use only oxalate as a growth substrate. This utilization reduces the concentration of soluble oxalate in the intestine and thus the amount of oxalate available for absorption.

In a specific embodiment, the subject invention provides materials and procedures for the delivery of *O. formigenes* to the intestinal tracts of persons who are at increased risk for oxalate related disease. These bacteria and their progeny replicate in the intestine and remove oxalate from the intestinal tract, thereby reducing the amount of oxalate available for absorption and thus reducing the risk for oxalate related disease.

In a further embodiment of the subject invention, a reduction in oxalate absorption is achieved by administering enzymes which act to degrade oxalate. These enzymes may be isolated and purified or they may be administered as a cell lysate of *Oxalobacter formigenes*. In a specific embodiment, the enzymes which are administered are formyl-CoA transferase and oxalyl-CoA decarboxylase. In a preferred embodiment, additional factors which improve enzyme activity can be administered. These additional factors may be, for example, oxalyl CoA, $MgCl_2$, and TPP (thiamine diphosphate, an active form of vitamin $B_1$).

A further aspect of the subject invention pertains to pharmaceutical compositions for oral administration. These compositions release the oxalate degrading microbes, or oxalate degrading enzymes, in the small intestine of humans. Preferably the microorganisms and/or enzymes are encapsulated in a dose delivery system that decreases the probability of release of the materials in the human stomach but increases the probability of release in the small intestine. The microorganisms and/or enzymes also may be administered as a constituent of foods, such as milk, meats, and yogurt.

DETAILED DISCLOSURE OF THE INVENTION

Figure 1A:
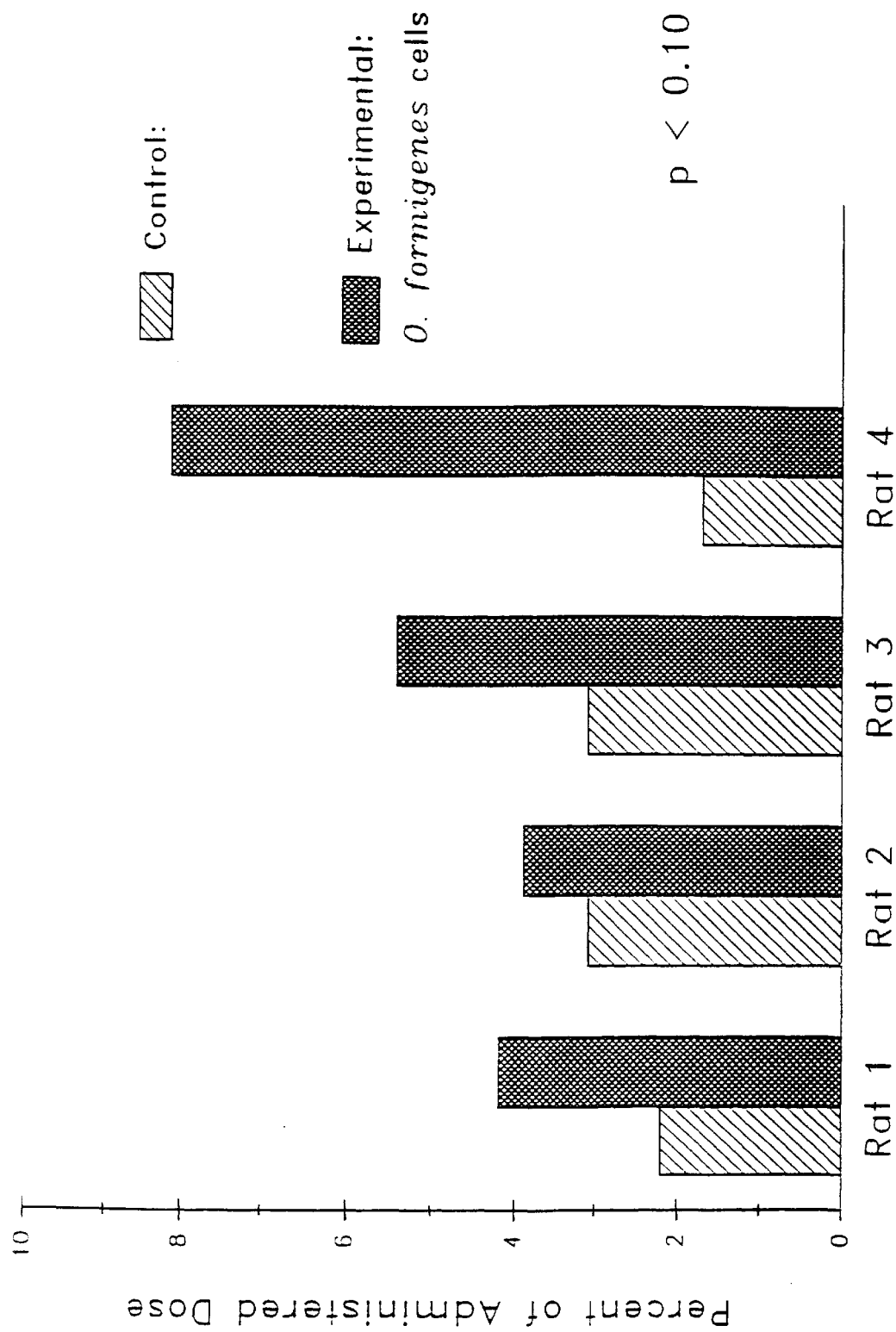
FIG. 1*a* shows the results of a study evaluating the fate of dietary oxalate when *Oxalobacter formigenes* cells are included in the diet.

The subject invention pertains to the introduction of oxalate-degrading bacteria and/or enzymes into the human intestinal tract where the activity of these materials reduces the absorption of oxalate and reduces the risk of disease due to oxalate.

In a specific embodiment, the subject invention pertains to the preparation and administration of cells of oxalate-degrading bacteria of the species, *Oxalobacter formigenes*, to the human intestinal tract where their metabolic activities reduce the amount of oxalate available for absorption from the intestine and thus reduce concentrations of oxalate in kidney and other cellular fluids. The introduced cells degrade oxalate and replicate in the intestinal habitat so that progeny of the initial cells colonize the intestine and continue to remove oxalate. This activity reduces the risk for formation of kidney stones as well as other disease complications caused by oxalic acid. In a preferred embodiment, the specific strains of *O. formigenes* used are strains isolated from human intestinal samples. The strains are thus part of the normal human intestinal bacterial flora. However, since they are not present in all persons, the introduction of these organisms corrects a deficiency that exists in some humans.

Enrichment of the contents of the small intestine with one or more species of oxalate-degrading bacteria causes a reduction of oxalate in the intestinal contents. Some of the bacteria carry out oxalate degradation at or near the site of absorption. The activity of the bacteria decreases the level of absorption of dietary oxalate.

Pharmaceutical compositions for the introduction of oxalate degrading bacteria and/or enzymes into the small intestine include bacteria and/or enzymes that have been lyophilized or frozen in liquid or paste form and encapsulated in a gel capsule. The gel cap material is preferably a polymeric material which forms a delivery pill or capsule that is resistant to degradation by the gastric acidity and pepsin of the stomach but is degraded with concomitant release of oxalate-degrading materials by the higher pH and bile acid contents in the proximal small intestine. The released material then converts oxalate present in the small intestine to harmless products. Pharmaceutical carriers also could be combined with the bacteria or enzymes. These would include saline-phosphate buffer.

Bacteria and/or enzymes to be administered can be delivered as capsules or microcapsules designed to protect the material from adverse effects of the acid stomach. One or more of several enteric protective coating methods can be used. Descriptions of such enteric coatings include the use of cellulose acetate phthalate (CAP) (Yacobi, A., E. H. Walega, 1988, Oral sustained release formulations: Dosing and evaluation, Pergammon Press). Other descriptions of encapsulation technology include U.S. Pat. No. 5,286,495, which is incorporated herein by reference.

Other methods of administration of these microorganisms and/or enzymes to the small intestine include adding the material directly to food sources. The bacteria may be added as freshly harvested cells, freeze dried cells, or otherwise protected cells. Foods may be supplemented with oxalate degrading organisms without affecting their taste or appearance. These foods may be, for example, yogurt, milk, peanut butter or chocolate. Upon ingestion, when the food products are being digested and absorbed by the small intestine, the microorganisms and/or enzymes degrade oxalate present in the small intestine thus preventing absorption of the oxalate into the blood stream.

Foods can be supplemented with oxalate degrading microorganisms. The microbes can be grown in media and separated from the media in a paste form by centrifugation. Traditional yogurt cultures obtained from any commercial dairy could be mixed with the oxalate degrading microbial culture. This mixture of cultures then can be added to the basic dairy yogurt premix without affecting taste or consistency. The yogurt then can be produced and packaged by using traditional commercial procedures. In another example, the oxalate degrading bacteria can be added to already produced yogurts.

Another example is to add the microbes to milk after it has been homogenized and sterilized. Such a method is currently used for adding the *Lactobacillus acidophilus* organisms to milk by the dairy industry. Any food source containing bacteria could be used by supplementing with oxalate degrading bacteria, such as cheese or meat products that have selected microorganisms added during processing.

The strains of bacteria (*O. formigenes*) used according to the subject invention are preferably pure cultures that are isolated from anaerobic cultures that have been inoculated with dilutions of intestinal contents from normal humans. A special calcium oxalate containing medium that allows detection of oxalate degrading colonies can be used. The purity of each strain can be assured through the use of at least two subsequent repetitive cloning steps.

Strains of *O. formigenes* useful according to the subject invention have been characterized based upon several tests, these include: patterns of cellular fatty acids, patterns of cellular proteins, DNA and RNA (Jensen and Allison, 1995), and responses to oligonucleotide probes (Sidhu et al. 1996). Two groups of these bacteria (Groups I and II, both existing within the present description of the species) have been described. Strains used have been selected based upon oxalate degrading capacity, and evidence of the ability to colonize the human intestinal tract. Strains selected include representatives of both Groups I and II of the species.

One embodiment of the present invention involves procedures for selection, preparation and administration of the appropriate oxalate-degrading bacteria to a diversity of subjects. Prominently, but not exclusively, these are persons which do not harbor these bacteria in their intestines. These non-colonized persons are identified using tests that allow for rapid and definitive detecting of *O. formigenes* even when the organisms are at relatively low concentrations in mixed bacterial populations such as are found in intestinal contents. The methods of the subject invention can also be used to treat individuals whose oxalate-degrading bacteria have been depleted due to, for example, antibiotic treatment or in post-operative situations. Bacteria which can be used according to the subject invention can be identified by at least two methods:

1) Oligonucleotide probes specific for these bacteria can be used; and/or

2) A culture test wherein an anaerobic medium with 10 mM oxalate is inoculated and after incubation at 37° C. for 1 to 7 days, the loss of oxalate is determined.

Pure cultures of *O. formigenes* strains can be grown in large fermenter batch cultures and cells can be harvested using techniques known to those skilled in the art. Cells from a selected single strain or mixtures of known strains can be treated as needed (e.g., freeze dried with trehalose or glycerol) to preserve viability and are then placed in capsules designed to protect the cells through their passage through the acid stomach (enteric coated capsules).

Cells are ingested in quantities and at intervals determined by the needs of individuals. In some cases a single, or periodic, use may be all that is needed and in other cases regular ingestion (e.g., with meals) may be needed.

The invention further pertains to administration to the human intestinal tract of oxalate-degrading products or enzymes prepared from *O. formigenes* cells. In one embodiment, oxalate degrading enzymes can be purified and prepared as a pharmaceutical composition for oral consumption. In a preferred embodiment, these enzymes are produced recombinantly. DNA sequences encoding these enzymes are known to those skilled in the art and are described in, for example, WO 98/16632. These sequences, or other sequences encoding oxalte-degrading proteins, can be expressed in a suitable host. The host may be, for example, *E. coli*. The expressed protein may be isolated, purified and administered as described herein. Alternatively, the recombinant host expressing the desired oxalate-degrading proteins may be administered. The recombinant host may be administered in either a viable or non-viable form. In another preferred embodiment, the enzymes are coated or otherwise formulated or modified to protect the enzymes so that they are not inactivated in the stomach, and are available to exert their oxalate-degrading activity in the small intestine. Examples of such formulations are known to those skilled in the art and are described in, for example, U.S. Pat. No. 5,286,495.

Following are examples which illustrate procedures for practicing the invention. These examples should not be construed as limiting.

EXAMPLE 1
Treatment of High Risk Patients

Enteric coated *O. formigenes* cells can be ingested by patient populations at high risk for oxalate related disease. These include:

1. Persons that have a history of urolithiasis with multiple episodes of idiopathic stone disease.
2. Persons at risk for urolithiasis with high urinary oxalate due to enteric disease (enteric-hyperoxaluria).
3. Persons with high serum oxalate levels due to end stage renal disease.
4. Persons with vulvar vestibultitis.
5. Persons that have diets with high levels of oxalate such as found in certain areas and seasons in India and in Saudi Arabia.

EXAMPLE 2
Treatment of Low Risk Patients

Enteric protected *O. formigenes* cells can also be ingested by individuals in populations at lower risk for oxalate related disease. These include:

1. Persons that have lost populations of normal oxalate degrading bacteria due to: treatments with oral antibiotics or bouts of diarrheal disease.
2. Infants will be inoculated so that a normal protective population of Oxalabacter will be more easily established than is the case later in life when competitive exclusion principles operate.
3. Other as yet unspecified persons who may benefit.

EXAMPLE 3
Use of Oxalate Degrading Enzymes From *Oxalobacter formigenes* to Control of Hyperoxaluria A study was conducted to evaluate the efficacy of oxalate degrading enzymes from *Oxalobacter formigenes* for the control of hyperoxaluria.

Animals Used: Male Sprague Dawley Rats: BW 250–300 g
Diets Used: Normal Diet (N.D.): Harlan Teklad TD 89222; 0.5% Ca, 0.4%P
Drug Used: Lyophilized mixture of *Oxalobacter formigenes* lysate (source of enzymes) with Oxalyl CoA, $MgCl_2$ and TPP.
Drug Delivery System (Capsules): Size 9 capsules for preclinical rat studies (Capsu-Gel). Enteric Coating EudragitL-100-55 (Hulls America, Inc.). Basal 24 hr urine collection. Fecal analysis for *Oxalobacter formigenes*—rats were not colonized with *Oxalobacter formigenes*.
Experimental Protocol
A. Long-term Studies
Animal Protocol
Group I (n=4): Fed oxalate diet with lysate. Rats were given two capsules everyday at 4:00 p.m. and oxalate diet overnight. Diet was removed during the day (8:00 a.m. to 4:00 p.m.)
Group II (n=4): Fed oxalate diet as described for Group I (Hyperoxaluric Controls).
24 hr urine samples were collected on Day 7 and Day 9 of the above treatment.

Data on the mean urinary oxalate concentration for the two groups of rats shown above indicated that feeding of Oxalobacter lysate lowered the urinary oxalate concentration in Group I rats as compared to the hyperoxaluric controls (Group II). The enzymes can not be active for a long duration in the gastrointestinal tract; therefore, short-term studies were performed as described below.
B. Short-term Studies
Animal Protocol
Group I (n=4): Fed 1 capsule at 8:00 a.m.; oxalate diet for two hours (rats were fasted overnight so that they eat well during this period) and 1 capsule at 10:00 a.m.
Group II (n=4): Oxalate diet for two hours as for Group I.
Urine was collected from all the animals for the next five-hour period and analyzed for oxalate concentration. This was performed on days 11, 12 and 15 of this study.

The results of this study show that feeding the Oxalobacter lysate produces a significant decrease in urinary oxalate levels in a 5 hour period after oxalate and drug administration in Group I rats as compared to the hyperoxaluric control group (Group II). At this point a crossover study between the two groups of rats was performed.
C. Cross-Over Studies
Animal Protocol
Group I: Fed oxalate diet twice a day at 8:00–10:00 a.m. and 3:00 p.m–5:00 p.m.
Group II: Fed 1 capsule twice a day before feeding the oxalate diet as for Group I. Short-term studies for the effect of oxalobacter lysate feeding on urinary oxalate levels were performed as described in Section-B above on day-2 and day-5 after the cross-over. Crossover studies show that previously hyperoxaluric Group II rats, which are now being fed the Oxalobacter lysate, show a decline in urinary oxalate levels. In contrast the Group-I rats revert to hyperoxaluria upon withdrawal of the drug.

EXAMPLE 4

Treatment with *Oxalobacter formigenes* Cells to Rats

A study was conducted to evaluate the fate of dietary oxalate when *Oxalobacter formigenes* cells are included in the diet.

Methods

Male Wistar rats were fed a normal calcium (1%), high oxalate (0.5%) diet, or a low calcium (0.02%), high oxalate diet (0.5%) diet during two separate experiments. $^{14}$C-oxalate (2.0 uCi) was given on day 1 and again on day 7 of the study. *Oxalobacter formigenes* cells (380 mg/d) were administered in rat drinking water on days 5–11. The fate of $^{14}$C from oxalate was measured based on analysis of $^{14}$C in feces, urine and expired air. The rats served as self controls and measurements during the control period (before Oxalobacter cells were fed) were made during days 1–4; during the experimental period (when bacterial cells were fed) measurements were made on days 7–11.

Results

Figure 1B:
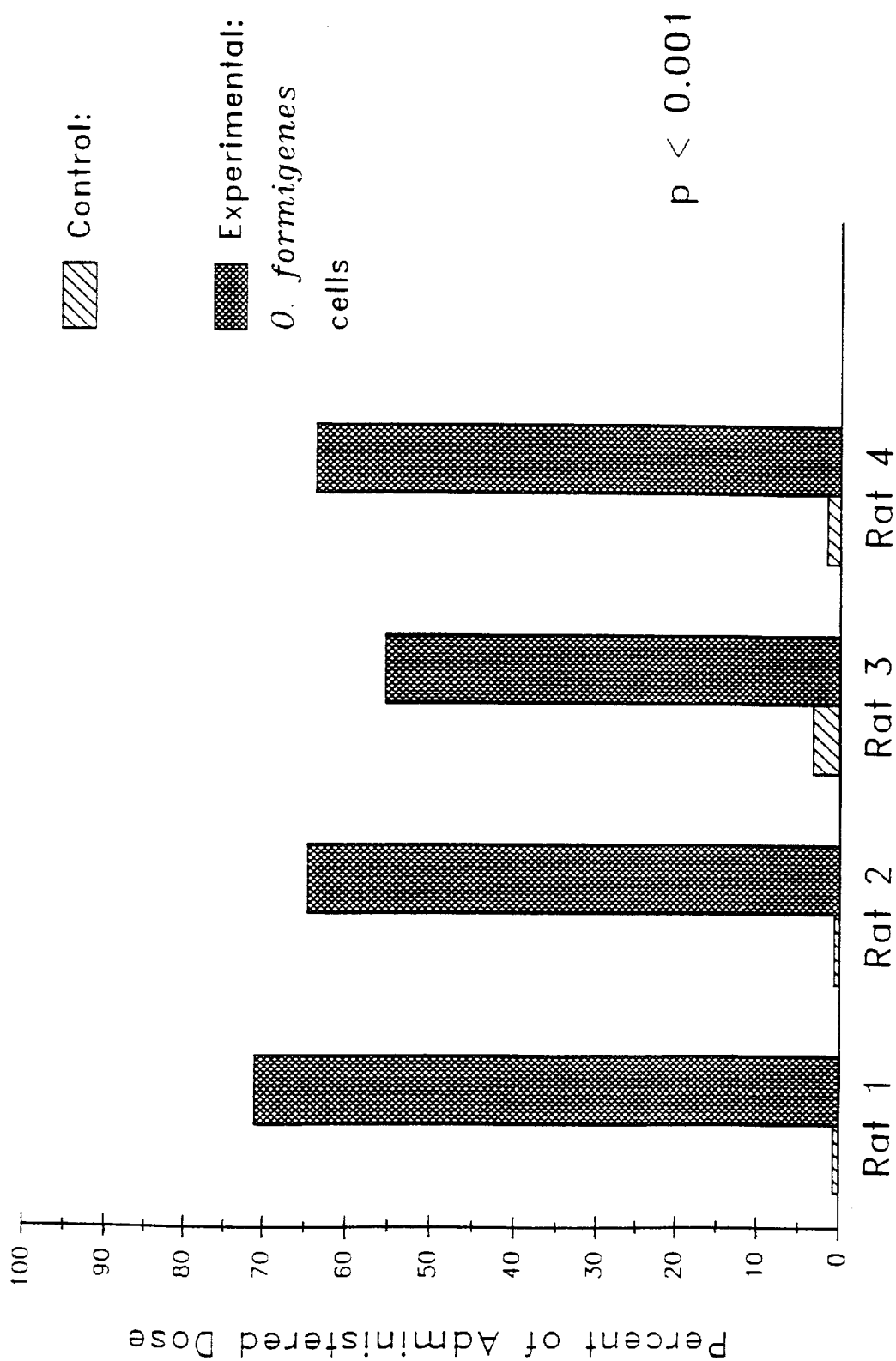
FIG. 1b shows the results of a study evaluating the fate of dietary oxalate when *Oxalobacter formigenes* cells are included in the diet.

1. When rats were fed the normal (1%) calcium diet, less than 1% of the administered dose of $^{14}$C from oxalate was recovered in expired air (as carbon dioxide produced from $^{14}$C oxalate in the intestine, absorbed into blood and then expired) however in all cases more of the $^{14}$C was recovered during the period when rats were fed Oxalobacter cells (FIG. 1a) This is in contrast to results obtained when the diet was low in calcium (0.02%) when more than 50% of the $^{14}$C from oxalate was recovered as carbon dioxide in expired air during the experimental period when rats were fed Oxalobacter cells (FIG. 1b). These results are strikingly different from the very low quantities of $^{14}$C (less than 5%) recovered during the control period (before the feeding of Oxalobacter cells). Thus feeding *Oxalobacter formigenes* cells to rats markedly increased the amount of dietary oxalate that was degraded in the intestinal tract.

Figure 2A:
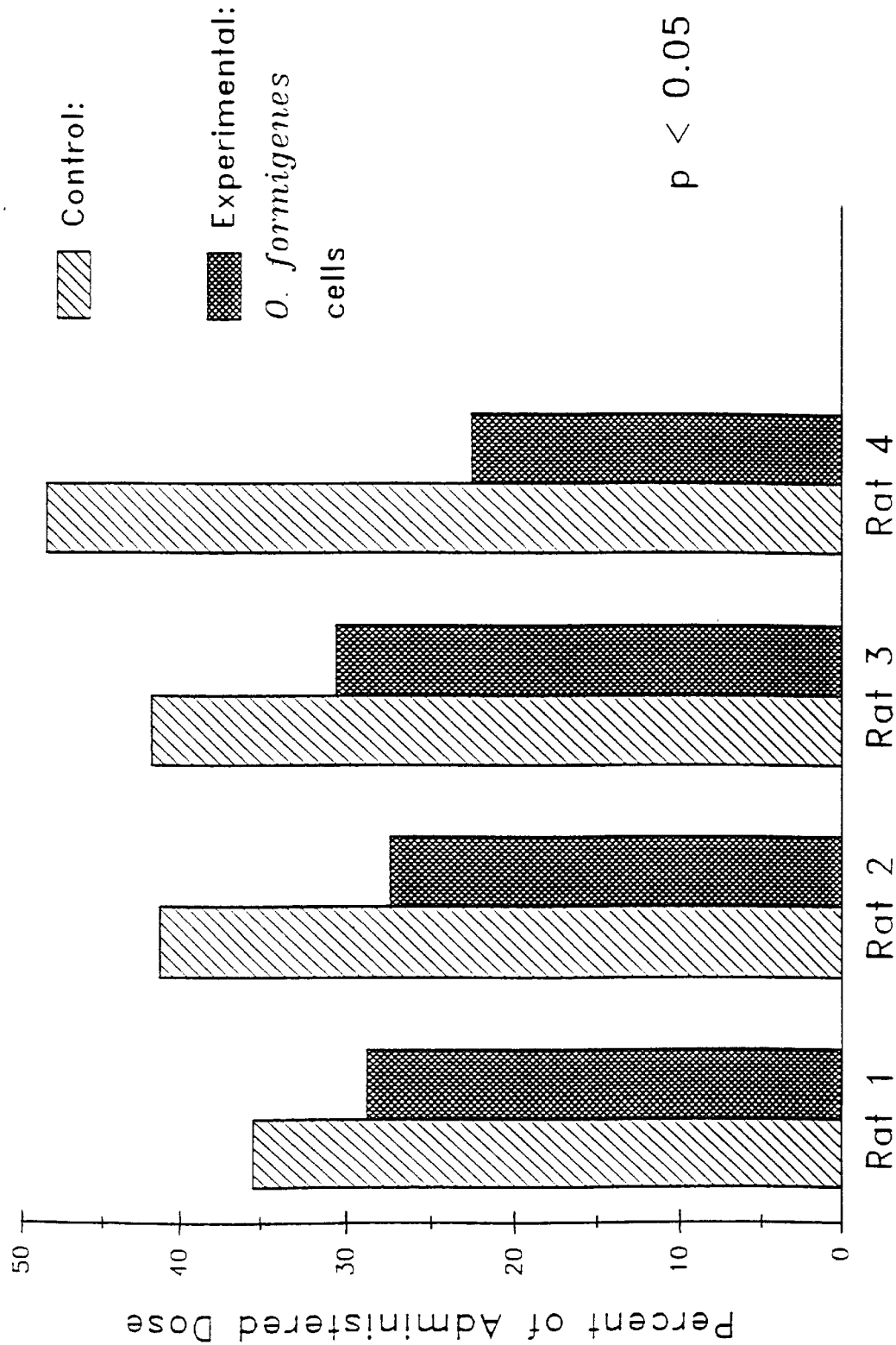
FIG. 2a shows the results of a study evaluating the fate of dietary oxalate when *Oxalobacter formigenes* cells are included in the diet.
Figure 2B:
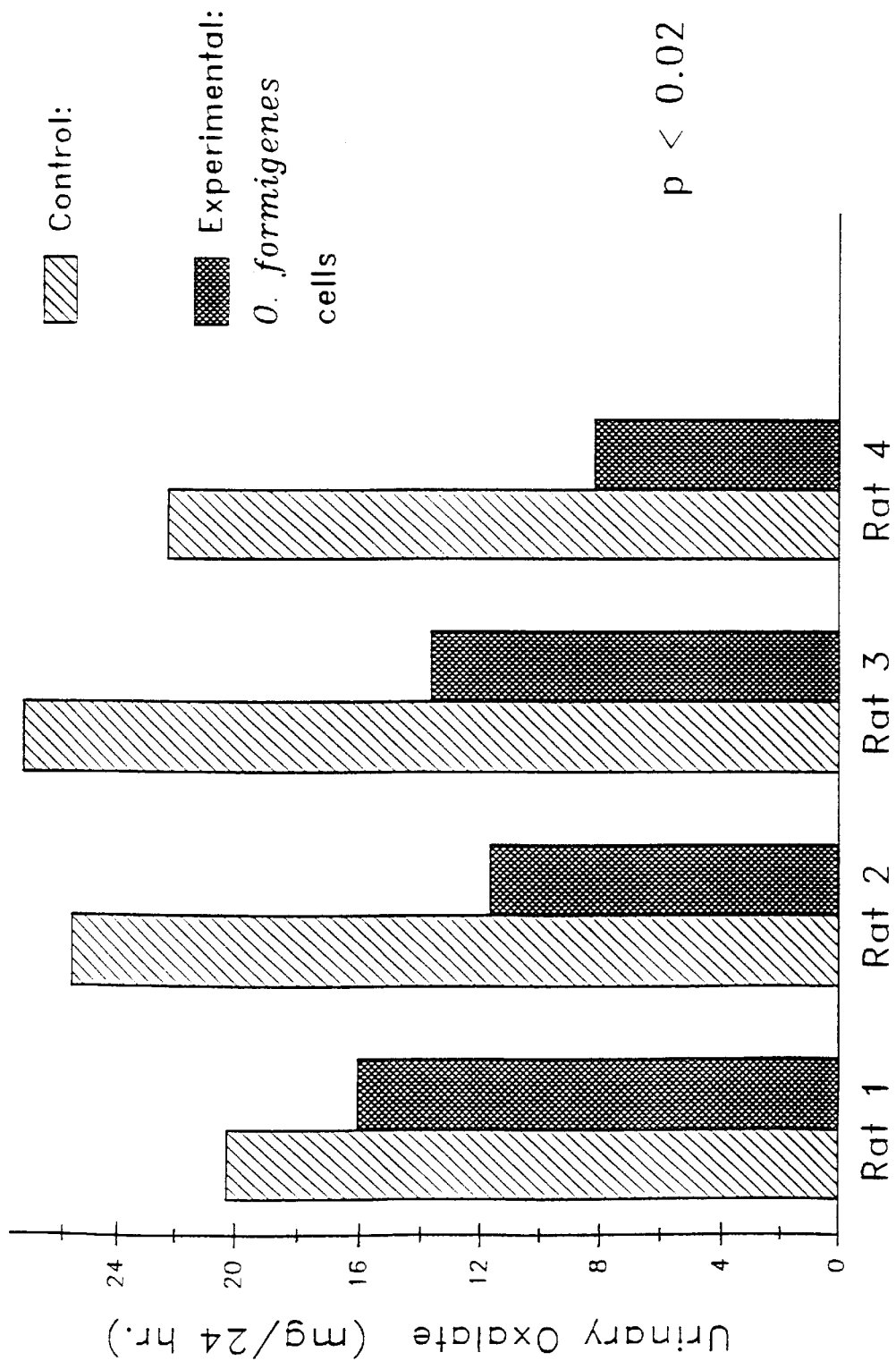
FIG. 2b shows the results of a study evaluating the fate of dietary oxalate when *Oxalobacter formigenes* cells are included in the diet.
Figure 2C:
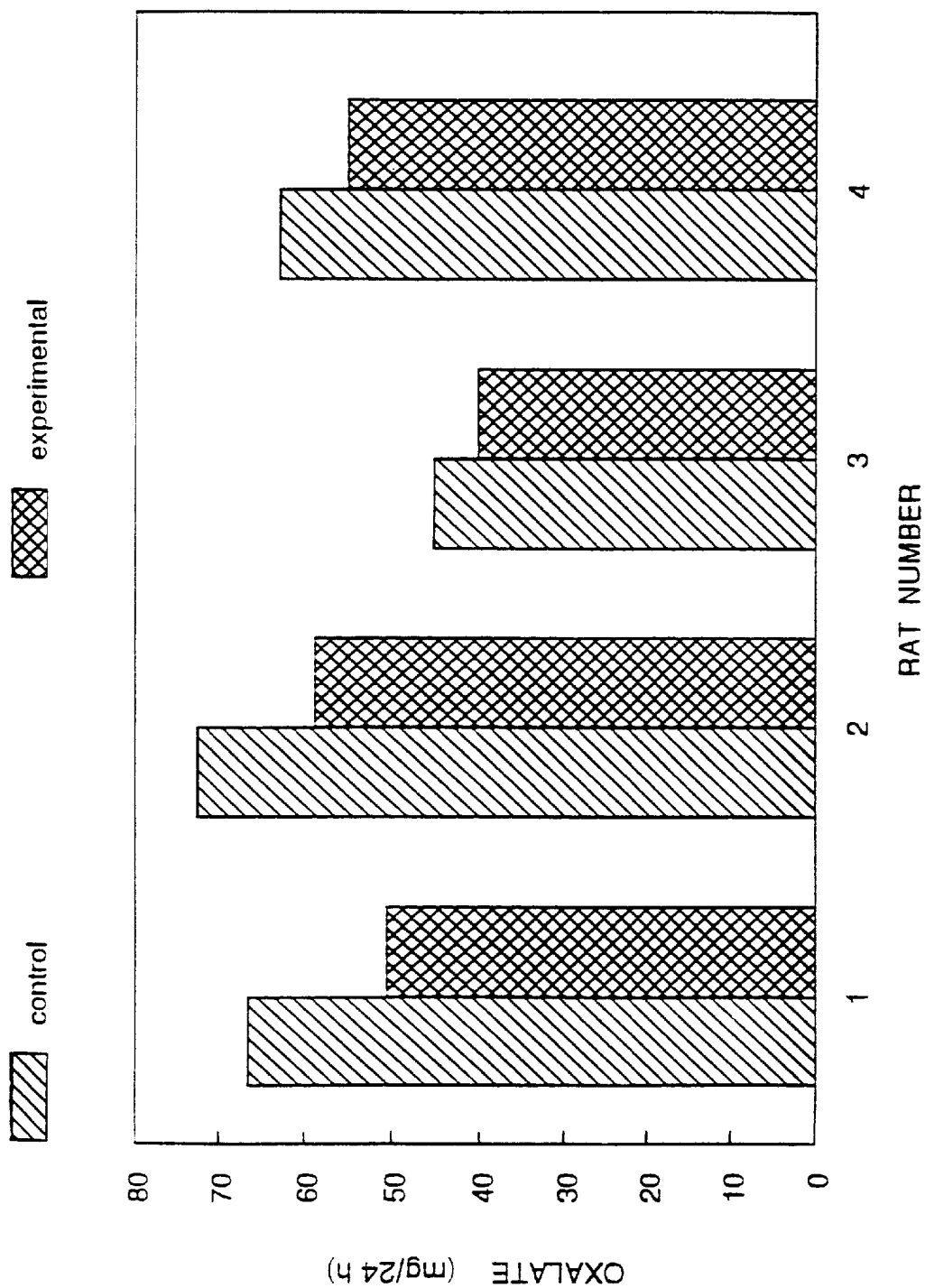
FIG. 2c shows the results of a study evaluating the fate of dietary oxalate when *Oxalobacter formigenes* cells are included in the diet.

2. Feeding Oxalobacter cells also decreased the amount of $^{14}$C-oxalate that was excreted in urine. Values for a 4 day collections during both the control and experimental periods and for a single day in each of these periods are shown in FIGS. 2a and 2b respectively. Quantities of oxalate recovered in rat feces were also lower during the experimental period (when Oxalobacter cells were fed) than was found for the control period (FIG. 2c).

Most laboratory rats do not carry Oxalobacter in their intestinal tracts (they are not colonized). The present results show that purposeful administration of these oxalate-degrading bacteria to rats causes a large portion of the dietary oxalate to be degraded and that consequently less of the oxalate from the diet is excreted in urine.

The effects of dietary calcium on oxalate degradation are marked. Calcium complexes with oxalate so that its solubility and availability for attack by Oxalobacter is limited and the amount that is degraded when rats are fed a high calcium diet is much less than amounts degraded when calcium in the diet is low.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Allison, M. J., H. M. Cook (1981) "Oxalate degradation by microbes of the large bowel of herbivores: the effect of dietary oxalate" *Science* 212:675–676.

Allison, M. J., K. A. Dawson, W. R. Mayberry, J. G. Foss (1985) "*Oxalabacter formigenes* gen. nov., sp. nov.: oxalate-degrading anaerobes that inhabit the gastrointestinal tract" *Arch. Microbiol.* 141:1–7.

Allison, M. J., H. M. Cook, D. B. Milne, S. Gallagher, R. V. Clayman (1986) "Oxalate degradation by gastrointestinal bacteria from humans" *J. Nutr.* 116:455–460.

Allison, M. J., S. L. Daniel, N. A. Cornick (1995) "Oxalate-degrading bacteria" In Khan, S. R. (ed.), *Calcium Oxalate in Biological Systems* CRC Press. (in press)

Costello, J., M. Smith, M. J. Allison "Manipulation of urinary oxalate by feeding Oxalobacter formigenes to rats and the possible significance of Oxalobacter in the extra-renal excretion of oxalate" (unpublished data).

Daniel, S. L., P. A. Hartman, M. J. Allison (1987) "Microbial degradation of oxalate in the gastrointestinal tracts of rats" *Appl. Environ. Microbiol.* 53:1793–1797.

Daniel, S. L., P. A. Hartman, M. J. Allison (1993) "Intestinal colonization of laboratory rats by anaerobic oxalate-degrading bacteria: effects on the urinary and fecal excretion of dietary oxalate" *Microbial Ecology in Health and Disease* 6:277–283.

Dawson, K. A., M. J. Allison, P. A. Hartman (1980) "Isolation and some characteristics of anaerobic oxalate-degrading bacteria the rumen" *Appl. Environ. Microbiol.* 40:833–839.

Doane, L. T., M. Liebman, D. R. Caldwell (1989) "Microbial oxalate degradation: effects on oxalate and calcium balance in humans" *Nutrition Research* 9:957–964.

Earnest, D. L. (1979) "Enteric hyperoxaluria" In Stollerman, G. H. (ed.), *Advances in internal medicine,* Year Book Medical Publisher, St. Louis, 25:407–427.

Hodgkinson, A. (1977) *Oxalic Acid in Biology and Medicine,* Academic Press, New York.

Ito, H. Miyake M., M. Noda "A new oxalate-degrading organism isolated from human feces" Abstr. Annual Meeting Amer. Soc. Microbiol., Q-106.

Jensen, N. S., M. J. Allison (1995) "Studies on the diversity among anaerobic oxalate degrading bacteria now in the species *Oxalobacter formigenes*" Abstr. to the General Meeting of the Amer. Soc. Microbiol., 1–29.

Solomons, C. C., M. H. Melmed S. M. Heitler (1991) "Calcium citrate for vulvar vestibulitis" *Journal of Reproductive Medicine* 36:879–882.

What is claimed is:

1. A method for reducing absorption of dietary oxalate in a human wherein said method comprises administering to said human a composition comprising a material selected from the group consisting of oxalate-degrading microbes and oxalate-degrading enzymes.

2. The method, according to claim 1, wherein said method comprises administration of oxalate-degrading enzymes.

3. The method, according to claim 2, which comprises administering formyl-CoA transferase and oxalyl-CoA decarboxylase.

4. The method, according to claim 3, wherein said enzymes are produced recombinantly.

5. The method, according to claim 3, which further comprises administering an additional factor selected from the group consisting of oxalyl CoA, $MgCl_2$ and TPP.

6. The method, according to claim 1, which comprises administering whole viable oxalate-degrading microbes.

7. The method, according to claim 6, wherein said microbes are *Oxalobacter formigenes.*

8. The method, according to claim 6, wherein said microbes colonize the intestines.

9. The method, according to claim 1, which is used to treat a patient whose intestines have insufficient numbers of oxalate-degrading bacteria.

10. The method, according to claim 9, which is used to treat a patient whose natural intestinal bacteria have been depleted due to treatment with antibiotics.

11. The method, according to claim 1, wherein said microbe or said enzyme is formulated to reduce inactivation in the stomach.

12. The method, according to claim 11, wherein said formulation comprises a coating which dissolves preferentially in the small intestine compared to the stomach.

* * * * *